United States Patent

Fitzlaff

Patent Number: 5,728,174
Date of Patent: Mar. 17, 1998

[54] SWING PHASE CONTROL FOR AN ARTIFICIAL KNEE JOINT

[75] Inventor: Gerhard Fitzlaff, VS-Schwenningen, Germany

[73] Assignee: Biedermann Motech GmbH, VS-Schwenningen, Germany

[21] Appl. No.: 532,627

[22] PCT Filed: Mar. 30, 1995

[86] PCT No.: PCT/EP95/01192

§ 371 Date: Oct. 3, 1995

§ 102(e) Date: Oct. 3, 1995

[87] PCT Pub. No.: WO95/27156

PCT Pub. Date: Oct. 12, 1995

[30] Foreign Application Priority Data

Mar. 31, 1994 [DE] Germany ............... 9405545 U

[51] Int. Cl.$^6$ ............................................. A61F 2/64
[52] U.S. Cl. ............................................. 623/46; 267/124
[58] Field of Search ................. 623/44, 43, 46, 623/25, 39–42; 188/322.22, 319, 315; 267/127, 129, 226, 113, 118, 124

[56] References Cited

U.S. PATENT DOCUMENTS

| | | | |
|---|---|---|---|
| 1,616,540 | 2/1927 | Morgan | 188/315 X |
| 1,962,319 | 6/1934 | McCormick | 188/319 |
| 2,379,750 | 7/1945 | Rossman | 188/315 X |
| 3,214,155 | 10/1965 | Leavell . | |
| 4,297,544 | 10/1981 | Priesemuth | 267/114 X |
| 4,632,228 | 12/1986 | Oster et al. | 188/322.22 |
| 4,693,343 | 9/1987 | Boyd | 188/322.17 |
| 4,693,454 | 9/1987 | Tsuchiya et al. | 267/226 |
| 5,062,857 | 11/1991 | Berringer et al. . | |

FOREIGN PATENT DOCUMENTS

| | | | |
|---|---|---|---|
| A-1095378 | 6/1955 | France . | |
| 1141311 | 12/1962 | Germany | 267/127 |
| 1074522 | 2/1984 | U.S.S.R. | 623/44 |
| A-982527 | 2/1965 | United Kingdom . | |
| A-2264348 | 8/1993 | United Kingdom . | |
| WO-A-94 07442 | 4/1994 | WIPO . | |

*Primary Examiner*—David H. Willse
*Attorney, Agent, or Firm*—George W. Neuner

[57] ABSTRACT

A swing phase control for an artificial knee joint is provided with a cylinder (1) having one end closed by a head member (2) and the other end closed by a base member (3), a piston reciprocally movable within the cylinder in axial direction thereof and having a piston rod (6) passing outwards through a bore provided in the head member (2) for connection with the thigh part of a prosthesis. The head member (2) comprises a channel (12) with a check valve (13) providing a communication of the ambient with a head side first chamber (9) defined by the piston (7). The first chamber (9) communicates through a throttle passage with the base side second chamber (10) defined by the piston (7). The base member (3) comprises a vent bore (23) connecting the second chamber (10) with the ambient and a first spring (22) biasing the piston (7) towards the head member (2). Thus the swing phase control has good damping properties for movement of different speed.

4 Claims, 2 Drawing Sheets

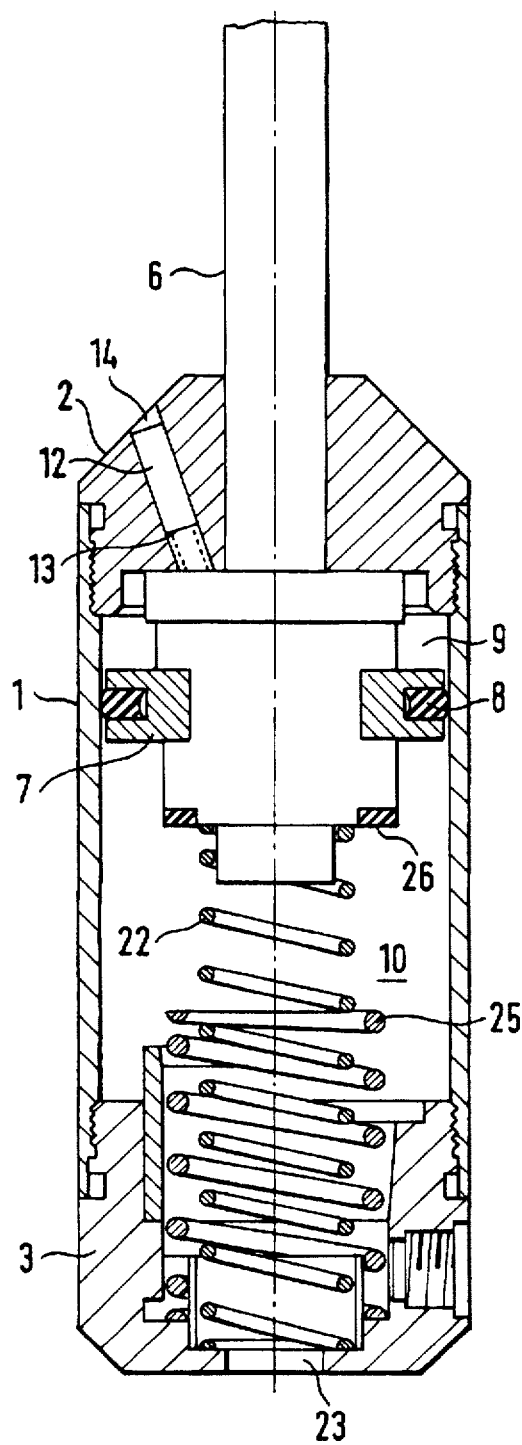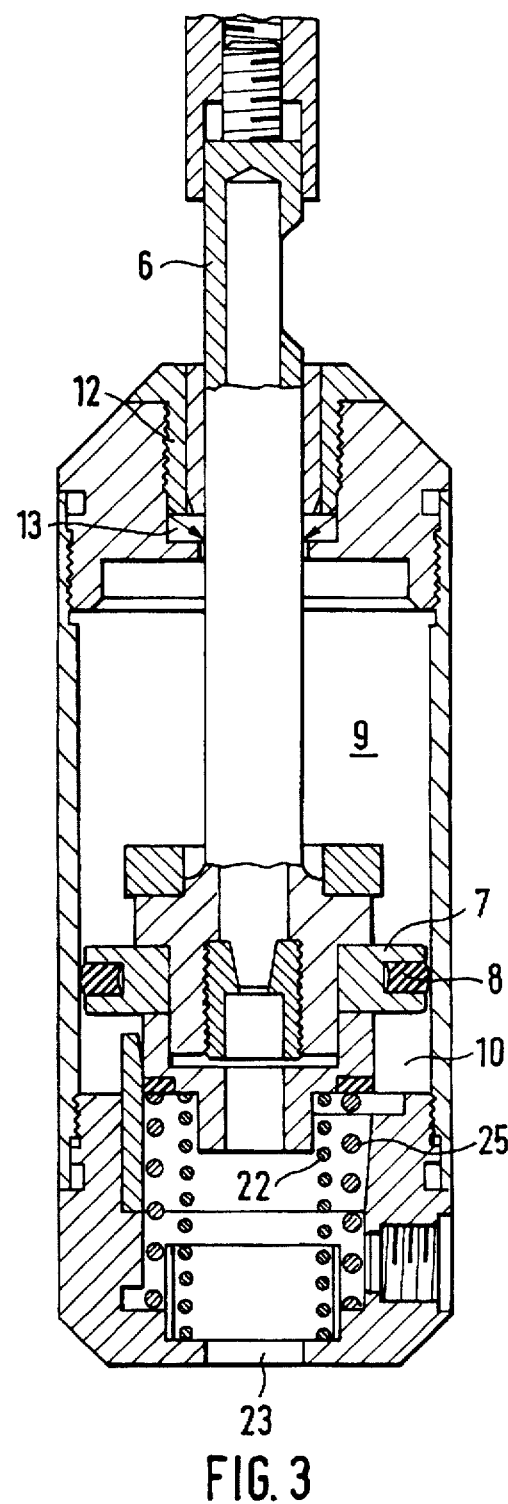

SWING PHASE CONTROL FOR AN ARTIFICIAL KNEE JOINT

The invention relates to a swing phase control for an artificial knee joint comprising a cylinder having one end closed by a head member and the other end closed by a base member, a piston reciprocally movable within the cylinder in axial direction thereof and having a piston rod passing outwards through a bore provided in the head member for connection with the thigh part of a prosthesis, a head side first chamber defined by the piston and a base side second chamber.

Such an apparatus is known from the U.S. Pat. No. 5,062,857.

It is the object of the invention to provide a swing phase control of the above defined kind which has good damping properties for movements of varying speed and nevertheless is of a simple construction.

This object is achieved by a swing phase control of the above defined kind which is characterized in that the head member comprises a channel connecting the first chamber with the ambient and including a check valve blocking the communication between the first chamber and the ambient, that the first and second chamber are connected through a throttle passage and that the base member comprises a vent bore connecting the second chamber with the ambient and a first spring biasing the piston towards the head member.

This solution provides for an extreme simple and light weight swing phase control.

According to a preferred embodiment a second spring having a shorter length of pass is provided for a second biasing stage. This accelerates the extension.

Further developments of the invention are defined in the sub-claims.

Further features and functionalities of the invention will be apparent from the description of embodiments with reference to the figures.

In the figures:

FIG. 2 shows a section through a second embodiment in a first operating position; and FIG. 3 shows the second embodiment in a second operating position.

Figure 1:
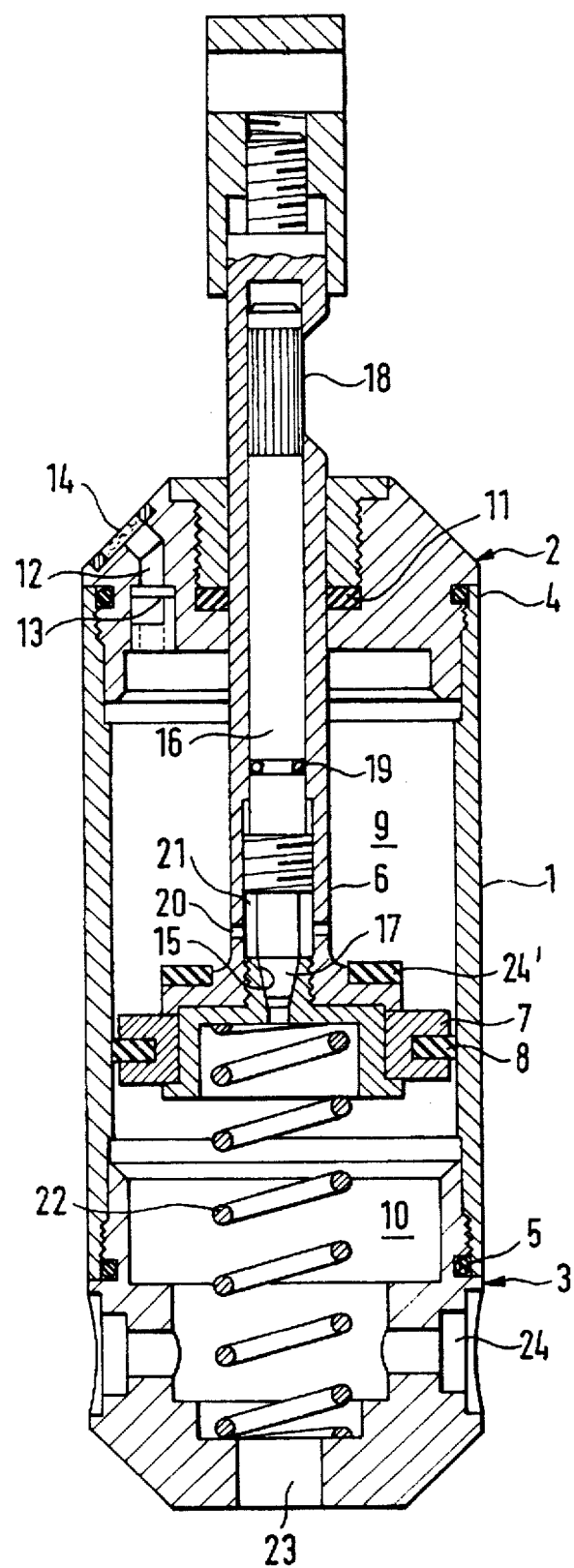
FIG. 1 shows a section through a first embodiment.

As best seen in FIG. 1 a second chamber 10 has a compression spring 22 provided coaxially therein and having a first end resting against an abutment face of the base member 3 and the opposite end resting on an abutment surface of the piston 7 for biasing the piston in a direction towards the head member 2. The second chamber 2 communicates with the ambient through a bore 23. Moreover, bores 24 are provided at the base member for connection with the lower leg. The piston 7 has an annular rubber cushion 24' provided on the top side thereof.

In operation the spring 22 dampens the flexional movement but accelerates the extensional movement. On the other hand, a dampening action is obtained by the air cushion developing within the first chamber 9. The dampening grade is determined by the axial position of the valve rod 16 or the cross section of the throttling passage defined thereby.

As best shown in FIG. 1 a channel formed as a bore 12 connecting the interior of the first chamber 9 with the ambient is provided in the head member 2. A check valve 13 formed as a flutter valve is arranged in the bore and formed to clear the communication from the ambient to the first chamber but to block the channel in opposite direction. The outside of the bore is covered by a dust filter 14. As shown in FIG. 1 the piston 7 has a coaxial bore 15 having a conical cross-section tapering towards and opening into the second chamber 10. The piston rod 6 is hollow and has a coaxially extending valve rod 16 disposed therein. The valve rod 16 has a shaft extending in axial direction and having an end at the bore 15 which has a conical portion 17 with a cone angle which is substantially equal to the angle of the conical bore 15. The valve rod is guided in a thread. The end of the valve rod opposite to the bore 15 has a knurled portion 18 which is accessible for adjusting the axial position of the valve rod. A seal 19 providing an outward seal is arranged between the access portion and the conical portion 17. The diameter of the valve rod in the portion thereof adjacent to the conical portion 17 is smaller than the inner diameter of the piston rod 6. This portion of the piston rod 6 is provided with bore 20 having a low air flow resistance and connecting the first chamber 9 with the adjacent interior 21 of the piston rod 6. By adjusting the valve rod 16 in axial direction a throttle passage having a predetermined cross-section and connecting the first chamber 9 with the second chamber 10 is defined between the wall of the bore 15 and the conical portion 17.

In FIGS. 2 and 3 a swing phase control corresponding to the above described embodiment is schematically shown. Corresponding parts are referenced by the same reference signs. The piston, the piston rod and the valve rod as well as the adjustment facilities are only schematically indicated but are structured as in the embodiment of FIG. 1. The embodiment shown in the FIGS. 2 and 3 distinguishes from the first embodiment only by having a second compression spring 25 having one end resting on an abutment of the base member 3. As shown in FIG. 2 the second compression spring 25 has a length extending along substantially half of the distance between an abutment surface 26 of the piston 7 in the uppermost extensional position shown in FIG. 2 and the opposite lowermost flexional position shown in FIG. 3.

The operation corresponds to that of the first embodiment. However, an additional flexional damping begins when the abutment surface 26 engages the second compression spring 25 and the additional second spring 25 accelerates the extension at the beginning thereof.

A piston 7 carried on a piston rod 6 is provided within the cylinder. The piston 7 has suitable seals 8 for separating the interior of the cylinder into a head side first chamber 9 and a base side second chamber 10. The piston rod 6 passes outwards through a coaxial bore provided in the head member 2 and has a lug at the free end thereof for connection with the thigh part of a prosthesis. The piston rod 6 slides in the coaxial bore. The first chamber 9 is sealed from the ambient by means of seals 11.

I claim:

1. A prosthesis swing phase control for a prosthesis having a thigh part and a lower leg part forming an artificial knee joint, the swing phase control comprising:

a cylinder having a first end and a second end, a head member closing said first end and having a through bore therein, a base member closing said second end, a piston provided for reciprocal movement within said cylinder, a head side first chamber defined between said piston and said head member, a base side second chamber defined between said piston and said base member, a piston rod connected to said piston and passing through said through bore for connection with said thigh part, a channel provided in said head member for connecting said first chamber to the ambient, a check valve in said channel blocking a communication from said first chamber to the ambient, throttle passage means connecting said first chamber with said second chamber, vent bore means provided in said base member for connecting said second chamber with the ambient, and spring means for biasing said piston towards said head member, wherein the swing phase control is configured to be connected with the prosthesis such that during a flexional movement of the prosthesis air can flow freely through said channel into said first chamber and said flexional movement is damped by said spring, and an extensional movement of the prosthesis is accelerated by said spring and said extensional movement is dampened by an air cushion developing within said first chamber.

2. The swing phase control of claim 1, comprising means for adjusting a cross-section of said throttle passage means.

3. The swing phase control of claim 1, wherein said throttle passage means is formed as a coaxial bore formed within said piston rod, said bore having a conical section tapering towards said second chamber, valve rod means cooperating with said bore being provided in the interior of said piston rod and means being provided for displaceably adjusting said valve rod in axial direction thereof.

4. The swing phase control of claim 1, comprising a second spring means for a second biasing stage, said second spring means having a shorter length of pass than said first spring means.

* * * * *